(12) United States Patent
Huang et al.

(10) Patent No.: US 10,339,262 B2
(45) Date of Patent: Jul. 2, 2019

(54) SYSTEM AND METHOD FOR DEFINING CARE AREAS IN REPEATING STRUCTURES OF DESIGN DATA

(71) Applicant: KLA-Tencor Corporation, Milpitas, CA (US)

(72) Inventors: Junqing Huang, Fremont, CA (US); Soren Konecky, Alameda, CA (US); Hucheng Lee, Cupertino, CA (US); Kenong Wu, Davis, CA (US); Lisheng Gao, Morgan Hill, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 37 days.

(21) Appl. No.: 15/351,813

(22) Filed: Nov. 15, 2016

(65) Prior Publication Data

US 2017/0286589 A1 Oct. 5, 2017

Related U.S. Application Data

(60) Provisional application No. 62/314,725, filed on Mar. 29, 2016.

(51) Int. Cl.
*G06F 17/50* (2006.01)
*G03F 7/00* (2006.01)
*G03F 7/20* (2006.01)
*G01N 21/95* (2006.01)

(52) U.S. Cl.
CPC ..... *G06F 17/5081* (2013.01); *G01N 21/9501* (2013.01); *G03F 7/7065* (2013.01)

(58) Field of Classification Search
None
See application file for complete search history.

(56) References Cited

U.S. PATENT DOCUMENTS

| | | | |
|---|---|---|---|
| 5,805,278 A | 9/1998 | Danko | |
| 6,614,924 B1* | 9/2003 | Aghajan | ............ G01N 21/9501 257/E21.53 |
| 6,621,570 B1 | 9/2003 | Danko | |
| 7,023,541 B2* | 4/2006 | Mizuo | ................ G01N 21/9501 356/237.4 |
| 7,092,082 B1 | 8/2006 | Dardzinski | |
| 7,135,344 B2* | 11/2006 | Nehmadi | .................. G03F 1/36 438/14 |

(Continued)

OTHER PUBLICATIONS

International Search Report dated Jun. 26, 2017 for PCT/US2017/024506.

*Primary Examiner* — Leigh M Garbowski
(74) *Attorney, Agent, or Firm* — Suiter Swantz pc llo

(57) ABSTRACT

A method includes identifying a first set of a first care area with a first sensitivity threshold, the first care area associated with a first design of interest within a block of repeating cells in design data; identifying an additional set of an additional care area with an additional sensitivity threshold, the additional care area associated with an additional design of interest within the block of repeating cells in design data; identifying one or more defects within the first set of the first care areas in one or more images of a selected region of a sample based on the first sensitivity threshold; and identifying one or more defects within the additional set of the additional care areas in the one or more images of the selected region of the sample based on the additional sensitivity threshold.

20 Claims, 5 Drawing Sheets

(56) References Cited

U.S. PATENT DOCUMENTS

| | | |
|---|---|---|
| 7,327,871 B2 | 2/2008 | Ishikawa |
| 7,570,796 B2 | 8/2009 | Zafar et al. |
| 7,676,077 B2 | 3/2010 | Kulkarni et al. |
| 7,715,997 B2 * | 5/2010 | Long ................. H01L 22/12 702/1 |
| 7,877,722 B2 * | 1/2011 | Duffy ................ G03F 7/7065 716/55 |
| 7,940,383 B2 * | 5/2011 | Noguchi ............. B82Y 15/00 356/237.2 |
| 8,559,001 B2 * | 10/2013 | Chang ............... G01N 21/9501 250/559.3 |
| 8,664,594 B1 | 4/2014 | Jiang et al. |
| 8,692,204 B2 | 4/2014 | Kojima et al. |
| 8,698,093 B1 | 4/2014 | Gubbens et al. |
| 8,716,662 B1 | 5/2014 | MacDonald et al. |
| 8,781,781 B2 * | 7/2014 | Kulkarni ........... G05B 23/0297 702/108 |
| 9,170,209 B1 * | 10/2015 | Chang ............... G01N 21/9501 |
| 9,171,364 B2 * | 10/2015 | Wu ..................... G06T 7/001 |
| 9,183,624 B2 | 11/2015 | Karsenti et al. |
| 9,286,675 B1 * | 3/2016 | Shabtay ............. G06T 7/0012 |
| 9,342,878 B2 * | 5/2016 | Yamaguchi ......... H01J 37/222 |
| 9,735,064 B2 * | 8/2017 | Lei ...................... H01L 22/00 |
| 2004/0218806 A1 | 11/2004 | Miyamoto et al. |
| 2006/0280358 A1 * | 12/2006 | Ishikawa .......... G01N 21/95607 382/149 |
| 2013/0028506 A1 | 1/2013 | Salter |
| 2013/0265408 A1 * | 10/2013 | Yamaguchi ......... H01J 37/222 348/80 |
| 2014/0105482 A1 * | 4/2014 | Wu ..................... G06T 7/001 382/149 |
| 2015/0012900 A1 | 1/2015 | Shifrin et al. |
| 2015/0048741 A1 | 2/2015 | Shortt et al. |
| 2015/0254394 A1 | 9/2015 | Hu et al. |
| 2015/0333471 A1 | 11/2015 | Chimmalgi et al. |
| 2015/0357179 A1 | 12/2015 | Wilson et al. |

* cited by examiner

SYSTEM AND METHOD FOR DEFINING CARE AREAS IN REPEATING STRUCTURES OF DESIGN DATA

PRIORITY

The present application claims priority under 35 U.S.C. § 119(e) to U.S. Provisional Patent Application Ser. No. 62/314,725, filed Mar. 29, 2016 entitled DEFINING CARE AREA IN REPEATING STRUCTURE BY USER DRAWING IN DESIGN VIEW, naming Junqing Huang, Soren Konecky, Hucheng Lee, Kenong Wu, and Lisheng Gao as inventors, which is incorporated herein by reference in the entirety.

TECHNICAL FIELD

The present invention generally relates to wafer inspection and review and, more particularly, to locating defects during wafer inspection with defined care areas in repeating structures of design data.

BACKGROUND

Fabricating semiconductor devices such as logic and memory devices typically includes processing a substrate such as a semiconductor wafer using a large number of semiconductor fabrication processes to form various features and multiple levels of the semiconductor devices. Multiple semiconductor devices may be fabricated in an arrangement on a single semiconductor wafer and then separated into individual semiconductor devices.

Semiconductor devices may develop defects during the fabrication processes. Inspection processes are performed at various steps during a semiconductor manufacturing process to detect defects on a specimen. Inspection processes are an important part of fabricating semiconductor devices such as integrated circuits, becoming even more important to successfully manufacture acceptable semiconductor devices as the dimensions of semiconductor devices decrease. Detection of defects has become highly desirable as the dimensions of semiconductor devices decrease, as even relatively small defects may cause unwanted aberrations in the semiconductor devices.

One method of defect detection includes comparing wafer inspection images to wafer design data, where the wafer design data includes one or more care areas. The care areas indicate designs of interest with potential to be a defect location. Known methods of defining care areas, however, can be labor and/or computational intensive. As such, it would be desirable to provide a solution for improved wafer inspection and defect classification to resolve manufacturing issues and provide improved wafer inspection capabilities.

SUMMARY

A system is disclosed, in accordance with one or more embodiments of the present disclosure. In one illustrative embodiment, the system includes an inspection tool. In another illustrative embodiment, the system includes a user interface. In another illustrative embodiment, the system includes a controller including one or more processors configured to execute a set of program instructions stored in memory. In another illustrative embodiment, the program instructions are configured to cause the one or more processors to receive design data. In another illustrative embodiment, the design data includes a block of repeating cells. In another illustrative embodiment, the program instructions are configured to cause the one or more processors to present, on the user interface, a particular cell of the block of repeating cells. In another illustrative embodiment, the program instructions are configured to cause the one or more processors to define a first care area associated with a first design of interest in the particular cell. In another illustrated embodiment, the first care area has a first sensitivity threshold. In another illustrative embodiment, the program instructions are configured to cause the one or more processors to define an additional care area associated with an additional design of interest in the particular cell. In another illustrative embodiment, the additional care area has an additional sensitivity threshold. In another illustrative embodiment, the program instructions are configured to cause the one or more processors to identify a set of first care areas within the block of repeating cells by performing a search function to identify additional occurrences of the first design of interest within the block of repeating cells. In another illustrative embodiment, the program instructions are configured to cause the one or more processors to identify a set of additional care areas within the block of repeating cells by performing a search function to identify additional occurrences of the additional design of interest within the block of repeating cells. In another illustrative embodiment, the program instructions are configured to cause the one or more processors to receive one or more images of a selected region of a sample from the inspection tool. In another illustrative embodiment, the program instructions are configured to cause the one or more processors to identify one or more defects within the first set of care areas in the one or more images of the selected region of the sample based on the first sensitivity threshold. In another illustrative embodiment, the program instructions are configured to cause the one or more processors to identify one or more defects within the additional set of care areas in the one or more images of the selected region of the sample based on the additional sensitivity threshold.

A system is disclosed, in accordance with one or more embodiments of the present disclosure. In one illustrative embodiment, the system includes an inspection tool. In another illustrative embodiment, the system includes a user interface. In another illustrative embodiment, the system includes a controller including one or more processors configured to execute a set of program instructions stored in memory. In another illustrative embodiment, the program instructions are configured to cause the one or more processors to receive design data. In another illustrative embodiment, the design data includes a block of repeating cells. In another illustrative embodiment, the program instructions are configured to cause the one or more processors to present, on the user interface, a particular cell of the block of repeating cells. In another illustrative embodiment, the program instructions are configured to cause the one or more processors to define a first care area associated with a first design of interest in the particular cell. In another illustrative embodiment, the first care area has a first sensitivity threshold. In another illustrative embodiment, the program instructions are configured to cause the one or more processors to define an additional care area associated with an additional design of interest in the particular cell. In another illustrative embodiment, the additional care area has an additional sensitivity threshold. In another illustrative embodiment, the program instructions are configured to cause the one or more processors to identify a set of first care areas within the block of repeating cells by performing a search function to identify additional occurrences of the first design of interest within the block of repeating cells. In another illustrative embodiment, the program instructions are configured to cause the one or more processors to identify a set of additional care areas within the block of repeating cells by performing a search function to identify additional occurrences of the additional design of interest within the block of repeating cells.

A system is disclosed, in accordance with the present disclosure. In one illustrative embodiment, the system includes an inspection tool. In another illustrative embodiment, the system includes a user interface. In another illustrative embodiment, the system includes a controller including one or more processors configured to execute a set of program instructions stored in memory. In another illustrative embodiment, the program instructions are configured to cause the one or more processors to identify a first set of a first care area. In another illustrative embodiment, the first care area is associated with a first design of interest within a block of repeating cells in design data. In another illustrative embodiment, the first care area has a first sensitivity threshold. In another illustrative embodiment, the program instructions are configured to cause the one or more processors to identify an additional set of an additional care area. In another illustrative embodiment, the additional care area is associated with an additional design of interest within the block of repeating cells in design data. In another illustrative embodiment, the additional care area has an additional sensitivity threshold. In another illustrative embodiment, the program instructions are configured to cause the one or more processors to receive one or more images of a selected region of a sample from the inspection tool. In another illustrative embodiment, the program instructions are configured to cause the one or more processors to identify one or more defects within the first set of the first care areas in the one or more images of the selected region of the sample based on the first sensitivity threshold. In another illustrative embodiment, the program instructions are configured to cause the one or more processors to identify one or more defects within the additional set of the additional care areas in the one or more images of the selected region of the sample based on the additional sensitivity threshold.

A method is disclosed, in accordance with one or more embodiments of the present disclosure. In one illustrative embodiment, the method may include, but is not limited to, receiving design data. In another illustrative embodiment, the design data includes a block of repeating cells. In another illustrative embodiment, the method may include, but is not limited to, presenting, on a user interface, a particular cell of the block of repeating cells. In another illustrative embodiment, the method may include, but is not limited to, defining a first care area associated with a first design of interest in the particular cell. In another illustrative embodiment, the first care area has a first sensitivity threshold. In another illustrative embodiment, the method may include, but is not limited to, defining an additional care area associated with an additional design of interest in the particular cell. In another illustrative embodiment, the additional care area has an additional sensitivity threshold. In another illustrative embodiment, the method may include, but is not limited to, identifying a set of first care areas within the block of repeating cells by performing a search function to identify additional occurrences of the first design of interest within the block of repeating cells. In another illustrative embodiment, the method may include, but is not limited to, identifying a set of additional care areas within the block of repeating cells by performing a search function to identify additional occurrences of the additional design of interest within the block of repeating cells. In another illustrative embodiment, the method may include, but is not limited to, receiving one or more images of a selected region of a sample from the inspection tool. In another illustrative embodiment, the method may include, but is not limited to, identifying one or more defects within the first set of care areas in the one or more images of the selected region of the sample based on the first sensitivity threshold. In another illustrative embodiment, the method may include, but is not limited to, identifying one or more defects within the additional set of care areas in the one or more images of the selected region of the sample based on the additional sensitivity threshold.

A method is disclosed, in accordance with one or more embodiments of the present disclosure. In one embodiment, the method may include, but is not limited to, receiving design data. In another illustrative embodiment, the design data includes a block of repeating cells. In another illustrative embodiment, the method may include, but is not limited to, presenting, on a user interface, a particular cell of the block of repeating cells. In another illustrative embodiment, the method may include, but is not limited to, defining a first care area associated with a first design of interest in the particular cell. In another illustrative embodiment, the first care area has a first sensitivity threshold. In another illustrative embodiment, the method may include, but is not limited to, defining an additional care area associated with an additional design of interest in the particular cell. In another illustrative embodiment, the additional care area has an additional sensitivity threshold. In another illustrative embodiment, the method may include, but is not limited to, identifying a set of first care areas within the block of repeating cells by performing a search function to identify additional occurrences of the first design of interest within the block of repeating cells. In another illustrative embodiment, the method may include, but is not limited to, identifying a set of additional care areas within the block of repeating cells by performing a search function to identify additional occurrences of the additional design of interest within the block of repeating cells.

A method is disclosed, in accordance with one or more embodiments of the present disclosure. In one illustrative embodiment, the method may include, but is not limited to, identifying a first set of a first care area. In another illustrative embodiment, the first care area is associated with a first design of interest within a block of repeating cells in design data. In another illustrative embodiment, the first care area has a first sensitivity threshold. In another illustrative embodiment, the method may include, but is not limited to, identifying an additional set of an additional care area. In another illustrative embodiment, the additional care area is associated with an additional design of interest within the block of repeating cells in design data. In another illustrative embodiment, the additional care area has an additional sensitivity threshold. In another illustrative embodiment, the method may include, but is not limited to, receiving one or more images of a selected region of a sample from the inspection tool. In another illustrative embodiment, the method may include, but is not limited to, identifying one or more defects within the first set of the first care areas in the one or more images of the selected region of the sample based on the first sensitivity threshold. In another illustrative embodiment, the method may include, but is not limited to, identifying one or more defects within the additional set of the additional care areas in the one or more images of the selected region of the sample based on the additional sensitivity threshold.

It is to be understood that both the foregoing general description and the following detailed description are exemplary and explanatory only and are not necessarily restrictive of the present disclosure. The accompanying drawings, which are incorporated in and constitute a part of the characteristic, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Figure 1:
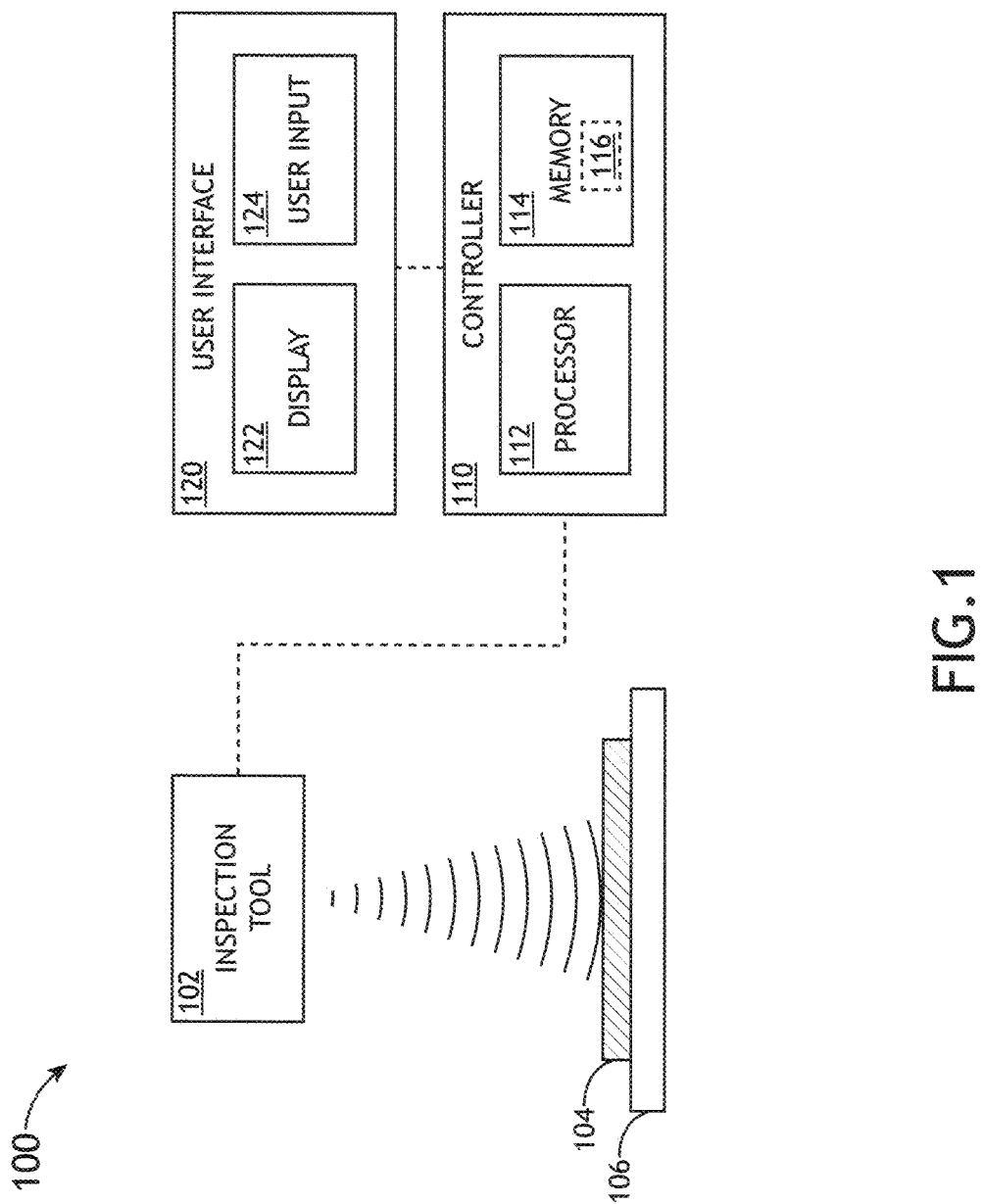
FIG. 1 illustrates a block diagram of a system for wafer inspection, in accordance with the present disclosure.
Figure 2A:
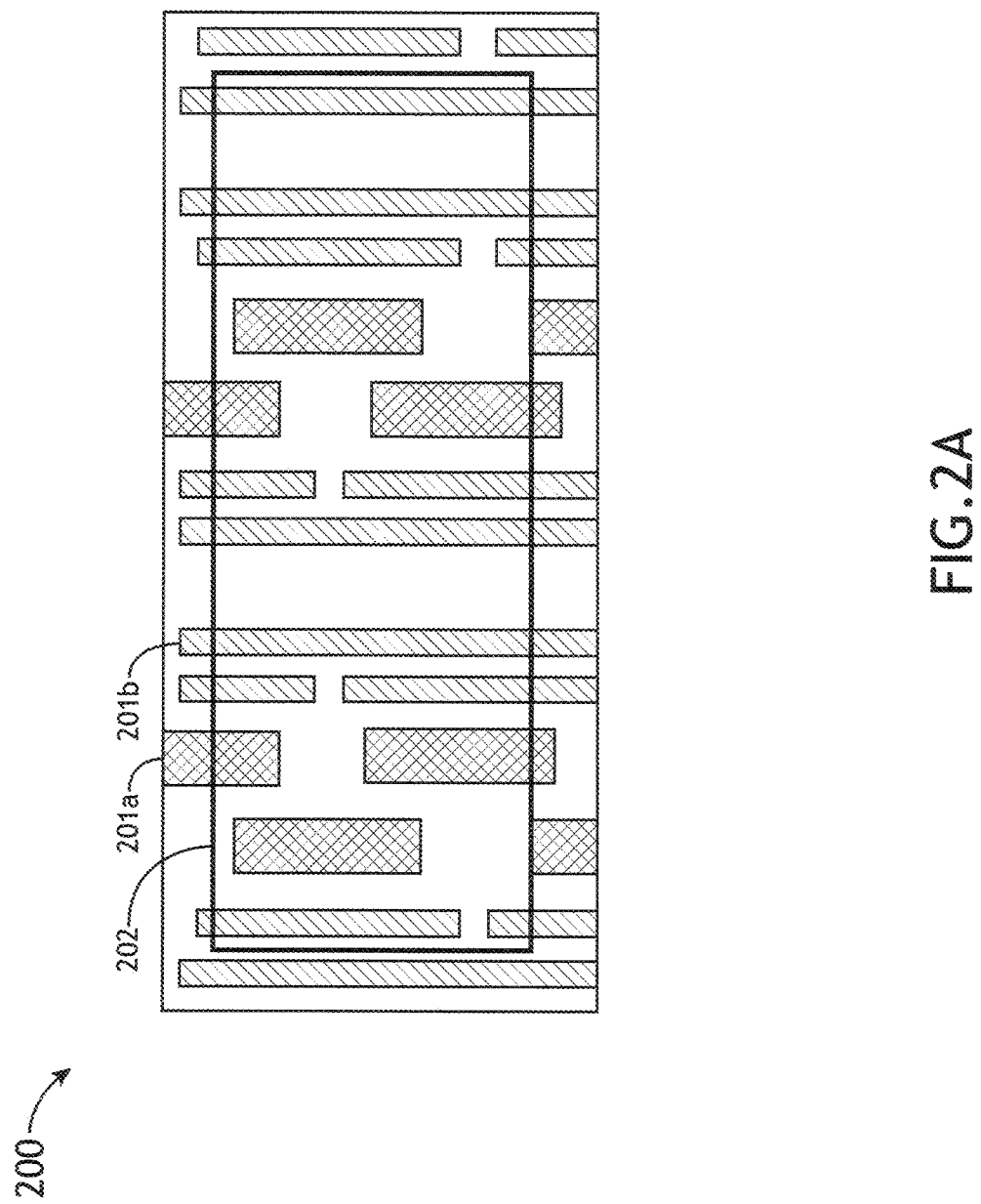
FIG. 2A illustrates a cell from a block of repeating cells in a set of design data, in accordance with the present disclosure.
Figure 2B:
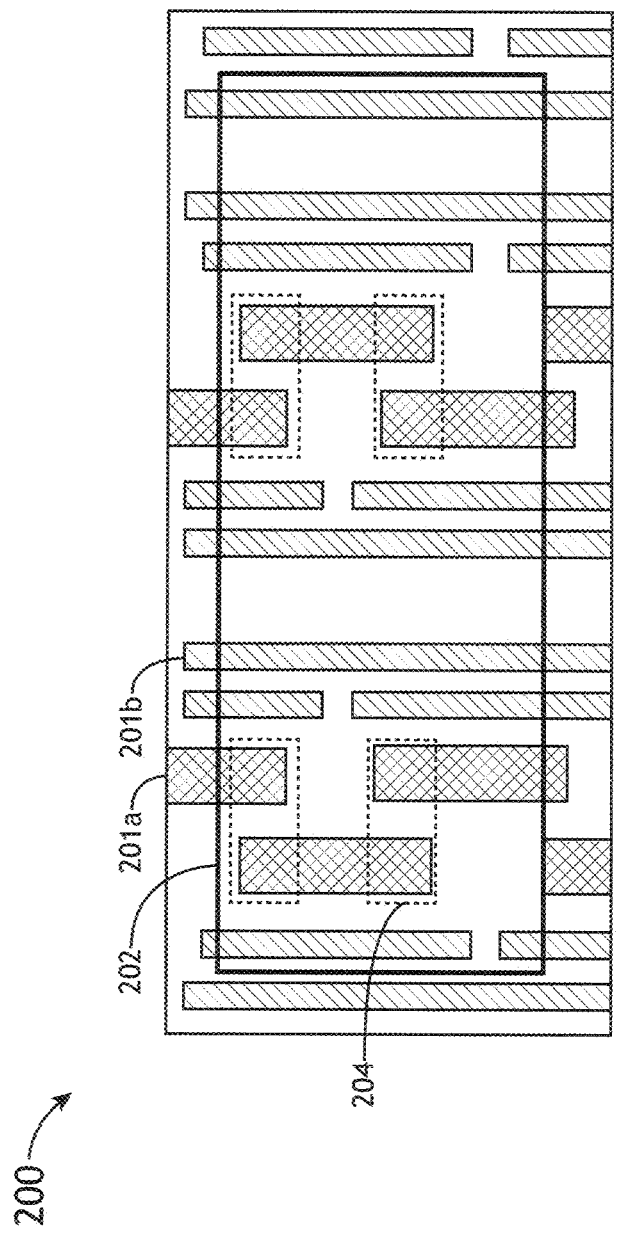
FIG. 2B illustrates a cell from a block of repeating cells in a set of design data, in accordance with the present disclosure.
Figure 2C:
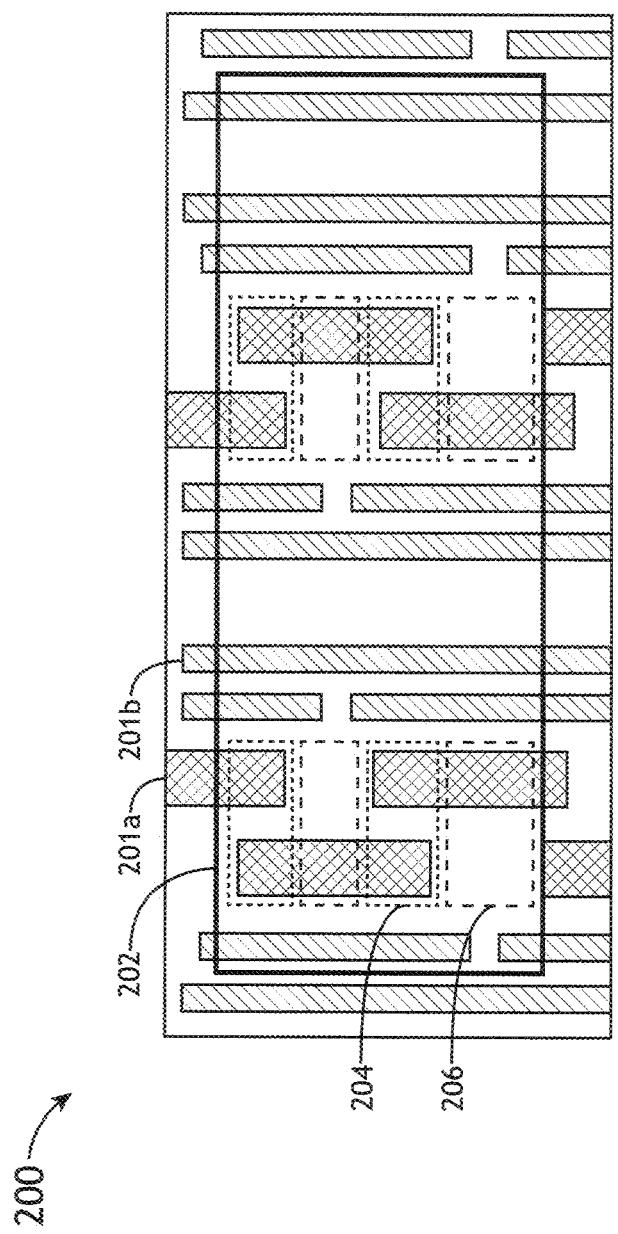
FIG. 2C illustrates a cell from a block of repeating cells in a set of design data, in accordance with the present disclosure.
Figure 3:
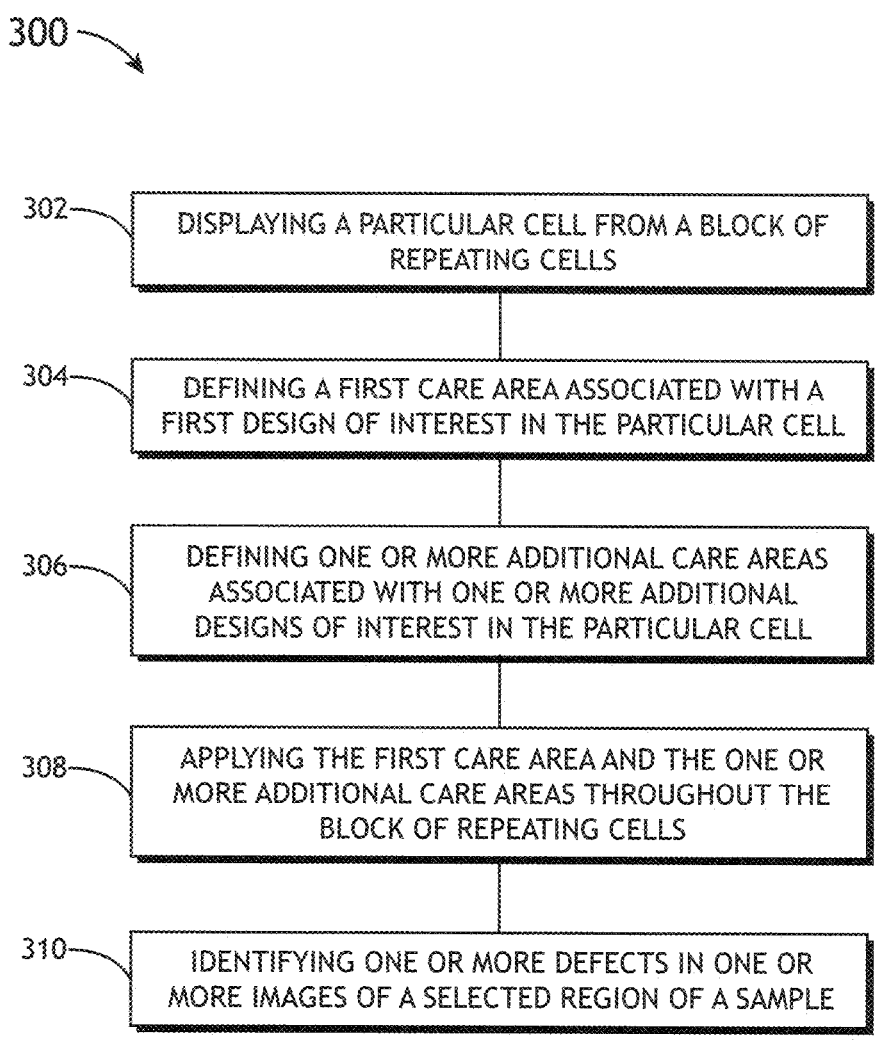
FIG. 3 illustrates a process flow diagram of a method for defining one or more defined care areas in a set of design data to identify one or more defects in one or more images of a selected region of a sample, in accordance with the present disclosure.

Referring generally to FIGS. 1 through 3, a method and system for defining one or more care areas associated with one or more designs of interest in repeating structures of design data are described, in accordance with one or more embodiments of the present disclosure.

Methods of defining care areas known in the art include Rutherford backscattering spectroscopy (RBS) rule generation from design data, design data pattern search, customer-provided process layer design, and manually drawing all care areas. These known methods, however, can be labor and/or computational intensive. For example, where the wafer design data includes too many care areas, a bottleneck occurs in the wafer inspection and review processes. Additionally, the known methods may require a defined electrical intent of the design (e.g. a power line, a ground line, a timing line, a word line, a bit line, a data line, a logic line, and the like) to create a desired care area or to align the care area-defined design data with the wafer inspection images. Where the required electrical intent is missing, defining care areas and/or aligning the design data to the wafer inspection images may not be possible. As such, embodiments of the present disclosure are directed to an improved system and method for defining one or more care areas in wafer design data for use in wafer inspection and review processes.

For purposes of the present disclosure, the terms "design" and "design data" as used herein generally refer to the physical design (layout) of an integrated circuit (IC) and data derived from the physical design through complex simulation or simple geometric and Boolean operations. For example, the physical design may be stored in a data structure such as a Graphic Data System (GDS) file, any other standard machine-readable file, any other suitable file known in the art, and a design database. IC layout data or chip design data is provided in a number of formats including, but not limited to, GDSII and OASIS formats. A GDSII file is one of a class of files used for the representation of design layout data. Other examples of such files include, but are not limited to, GL1 and OASIS files and proprietary file formats such as Reticle Design File (RDF) data, which is proprietary to KLA-Tencor, Milpitas, Calif. ("KT").

Design data is encoded with the manufacturing, logical, and electrical intent of the particular chip. Design data may be an output of Electronic Design Automation (EDA) tools. For example, the design data output from EDA tools may be processed by analysis software and converted to RDF format.

It is noted herein an image of a reticle acquired by a reticle inspection system and/or derivatives thereof may be used as a "proxy" or "proxies" for the design. Such a reticle image or a derivative thereof may serve as a substitute for the design layout in any embodiments described herein that use a design. The design may include any other design data or design data proxies described in U.S. Pat. No. 7,570,796, issued on Aug. 4, 2009; and U.S. Pat. No. 7,676,077, issued on Mar. 9, 2010, both of which are incorporated by reference in the entirety. In addition, the design data may be standard cell library data, integrated layout data, design data for one or more layers, derivatives of the design data, and full or partial chip design data.

It is further noted herein that simulated or acquired images from a wafer or reticle may be used as a proxy for the design. Image analysis may also be used as a proxy for design analysis. For example, shapes or polygons in the design may be extracted from an image of a design printed on a wafer and/or reticle, assuming that the image of the wafer and/or reticle is acquired with sufficient resolution to adequately image the polygons of the design.

FIG. 1 illustrates a system 100 for sample inspection, in accordance with one or more embodiments of the present disclosure. In one embodiment, the system 100 includes an inspection tool 102. In another embodiment, the system 100 includes a sample stage 106 for securing a sample 104. In another embodiment, the system 100 includes a controller 110. In another embodiment, the system 100 includes a user interface 120.

In another embodiment, the inspection tool 102 is configured to detect one or more defects of the sample 104. For example, the inspection tool 102 may include any appropriate characterization tool known in the art such as, but not limited to, an inspection tool or review tool. For example, the inspection tool 102 may include, but is not limited to, an electron beam inspection or review tool (e.g., SEM system). By way of another example, the inspection tool 102 may include, but is not limited to, an optical inspection tool. For instance, the optical inspection tool may include a broadband inspection tool including, but not limited to, a laser sustained plasma (LSP) based inspection tool. Additionally, the optical inspection tool may include a narrowband inspection tool, such as, but not limited to, a laser scanning inspection tool. Further, the optical inspection tool may include, but is not limited to, a brightfield imaging tool, or a darkfield imaging tool. It is noted herein that the inspection tool 102 may include any optical system configured to collect and analyze illumination reflected, scattered, diffracted, and/or radiated from a surface of a sample 104. Examples of inspection tools are described generally in U.S. Pat. No. 7,092,082, issued on Aug. 8, 2006; U.S. Pat. No. 6,621,570 issued on Sep. 16, 2003; and U.S. Pat. No. 5,805,278 issued on Sep. 9, 1998, which are each herein incorporated by reference in the entirety. Example of inspection tools are also described generally in U.S. Pat. No. 8,664,594, issued on Apr. 4, 2014; U.S. Pat. No. 8,692,204, issued on Apr. 8, 2014; U.S. Pat. No. 8,698,093, issued on Apr. 15, 2014; U.S. Pat. No. 8,716,662, issued on May 6, 2014; U.S. patent application Ser. No. 14/699,781, filed on Apr. 29, 2015; U.S. patent application Ser. No. 14/667,235, filed on Mar. 24, 2015; and U.S. patent application Ser. No. 14/459,155, filed on Aug. 13, 2014, which are each herein incorporated by reference in the entirety.

For purposes of the present disclosure, a defect may be classified as a void, short, particle, residue, scum, or any other defect known in the art.

In another embodiment, although not shown, the inspection tool 102 may include an illumination source, a detector and various optical components for performing inspection (e.g., lenses, beam splitters and the like). For example, the illumination source of the inspection tool 102 may include any illumination source known in the art. For instance, the illumination source may include, but is not limited to, a broadband light source or a narrowband light source. In addition, the illumination source may be configured to direct light to the surface of the sample 104 (via various optical components) disposed on the sample stage 106. Further, the various optical components of the inspection tool 102 may be configured to direct light reflected and/or scattered from the surface of the sample 104 to the detector of the inspection tool 102. By way of another example, the detector of the inspection tool 102 may include any appropriate detector known in the art. For instance, the detector may include, but is not limited to, a photo-multiplier tubes (PMTs), charge coupled devices (CCDs), time delay integration (TDI) camera, and the like. In addition, the output of the detector may be communicatively coupled to a controller 110, described in detail further herein.

In one embodiment, the sample 104 includes a wafer. For example, the sample 104 may include, but is not limited to, a semiconductor wafer. As used through the present disclosure, the term "wafer" generally refers to a substrate formed of a semiconductor and/or non-semi-conductor material. For instance, a semiconductor or semiconductor material may include, but is not limited to, monocrystalline silicon, gallium arsenide, and indium phosphide.

In another embodiment, the sample 104 is manufactured using one or more sets of design data. In another embodiment, a set of design data includes one or more sets of layers. For example, such layers may include, but are not limited to, a resist, a dielectric material, a conductive material, and a semi-conductive material. Many different types of such layers are known in the art, and the term wafer as used herein is intended to encompass a wafer on which all types of such layers may be formed. By way of another example, the one or more layers formed on the wafer may be repeated one or more times within the wafer. Formation and processing of such layers of material may ultimately result in completed devices. Many different types of devices may be formed on a wafer, and the term wafer as used herein is intended to encompass a wafer on which any type of device known in the art is being fabricated.

In another embodiment, a layer includes one or more cells. For example, the one or more cells may be repeated one or more times within the layer. By way of another example, cells may be regularly- or irregularly-shaped. It is noted herein a cell may be repeated between multiple layers of the one or more sets of design data.

In another embodiment, the one or more sets of design data include one or more designs of interest. For example, the one or more designs of interest may be repeated one or more times within the one or more sets of design data. In another embodiment, a design of interest may be associated with a cell located within the one or more sets of design data. It is noted herein a design of interest may correspond to a particular electrical intent of the one or more sets of design data. As used throughout the present disclosure, electrical intent of the one or more sets of design data includes, but is not limited to, a power line, a ground line, a timing line, a word line, a bit line, a data line, a logic line, and the like.

In another embodiment, the sample stage 106 may include any appropriate mechanical and/or robotic assembly known in the art. For example, the sample stage 106 may be configured to actuate the sample 104 to a selected position or orientation. For instance, the sample stage 106 may include or may be mechanically coupled to one or more actuators, such as a motor or servo, configured to translate or rotate the sample 104 for positioning, focusing, and/or scanning in accordance with a selected inspection or metrology algorithm, several of which are known to the art.

In one embodiment, the controller 110 includes one or more processors 112 and a memory medium 114. In another embodiment, one or more sets of program instructions 116 or stored in memory medium 114. In another embodiment, the one or more processors 112 are configured to execute the sets of program instructions 116 to carry out one or more of the various steps described throughout the present disclosure.

In another embodiment, the user interface 120 is communicatively coupled to the one or more processors 112 of controller 110. In another embodiment, the user interface 120 includes a display device 122. In another embodiment, the user interface 120 includes a user input 124.

In another embodiment, the controller 110 is configured to receive and/or acquire data or information from other systems or sub-systems (e.g., one or more sets of information from the inspection tool 102 or from any of the components of the inspection tool 102, or one or more user inputs received via the user interface 120) by a transmission medium that may include wireline and/or wireless portions. In another embodiment, the controller 110 of the system 100 is configured to transmit data or information (e.g., the output of one or more processes disclosed herein) to one or more systems or sub-systems (e.g., one or more commands to the inspection tool 102 or to any of the components of the inspection tool 102, or one or more outputs displayed on the user interface 120) by a transmission medium that may include wireline and/or wireless portions. In this regard, the transmission medium may serve as a data link between the controller 110 and other subsystems of the system 100. In another embodiment, the controller 110 is configured to send data to external systems via a transmission medium (e.g., network connection).

In one example, a detector of the inspection tool 102 may be coupled to the controller 110 in any suitable manner (e.g., by one or more transmission media indicated by the dotted line shown in FIG. 1) such that the controller 110 may receive the output generated by the detector. By way of another example, if the inspection tool 102 includes more than one detector, the controller 110 may be coupled to the multiple detectors as described above. It is noted herein the controller 110 may be configured to detect one or more defects of the sample 104 using detection data collected and transmitted by the inspection tool 102, utilizing any method and/or algorithm known in the art to detect defects on the wafer. For example, the inspection tool 102 may be configured to accept instructions from another subsystem of the system 100 including, but not limited to, controller 110. Upon receiving the instructions from the controller 110, the inspection tool 102 may perform an inspection process at the locations of the sample 104 identified in the provided instructions (i.e., the inspection recipe), transmitting the results of the inspection process to the controller 110.

In one embodiment, the set of program instructions 116 are programmed to cause the one or more processors 112 to identify one or more care areas in a block of repeating cells in design data, and additionally to identify one or more defects in one or more care areas in one or more images of a selected region of the sample 104. For example, the set of program instructions 116 may be programmed to cause the one or more processors 112 to receive design data, where the design data includes a block of repeating cells. By way of another example, the set of program instructions 116 may be programmed to cause the one or more processors 112 to present, on the user interface 120, a particular cell of the block of repeating cells. By way of another example, the set of program instructions 116 may be programmed to cause the one or more processors 112 to define a first care area associated with a first design of interest in the particular cell, where the first care area has a first sensitivity threshold. By way of another example, the set of program instructions 116 may be programmed to cause the one or more processors 112 to define an additional care area associated with an additional design of interest in the particular cell, where the additional care area has an additional sensitivity threshold. By way of another example, the set of program instructions 116 may be programmed to cause the one or more processors 112 to identify a set of first care areas within the block of repeating cells by performing a search function to identify additional occurrences of the first design of interest within the block of repeating cells. By way of another example, the set of program instructions 116 may be programmed to cause the one or more processors 112 to identify a set of additional care areas within the block of repeating cells by performing a search function to identify additional occurrences of the additional design of interest within the block of repeating cells. By way of another example, the set of program instructions 116 may be programmed to cause the one or more processors 112 to receive one or more images of a selected region of a sample 104 from the inspection tool. By way of another example, the set of program instructions 116 may be programmed to cause the one or more processors 112 to identify one or more defects within the first set of care areas in the one or more images of the selected region of the sample 104 based on the first sensitivity threshold. By way of another example, the set of program instructions 116 may be programmed to cause the one or more processors 112 to identify one or more defects within the additional set of care areas in the one or more images of the selected region of the sample 104 based on the additional sensitivity threshold. It is noted sensitivity thresholds of care areas are described in detail further herein.

In another embodiment, the set of programs instructions 116 are programmed to cause the one or more processors 112 to identify one or more care areas in a block of repeating cells of design data. For example, the set of program instructions 116 may be programmed to cause the one or more processors 112 to receive design data, where the design data includes a block of repeating cells. By way of another example, the set of program instructions 116 may be programmed to cause the one or more processors 112 to present, on the user interface 120, a particular cell of the block of repeating cells. By way of another example, the set of program instructions 116 may be programmed to cause the one or more processors 112 to define a first care area associated with a first design of interest in the particular cell, where the first care area has a first sensitivity threshold. By way of another example, the set of program instructions 116 may be programmed to cause the one or more processors 112 to define an additional care area associated with an additional design of interest in the particular cell, where the additional care area has an additional sensitivity threshold. By way of another example, the set of program instructions 116 may be programmed to cause the one or more processors 112 to identify a set of first care areas within the block of repeating cells by performing a search function to identify additional occurrences of the first design of interest within the block of repeating cells. By way of another example, the set of program instructions 116 may be programmed to cause the one or more processors 112 to identify a set of additional care areas within the block of repeating cells by performing a search function to identify additional occurrences of the additional design of interest within the block of repeating cells. It is noted sensitivity thresholds of care areas are described in detail further herein.

In another embodiment, the set of program instructions 116 are programmed to cause the one or more processors 112 to identify one or more defects in one or more care areas in one or more images of a selected region of the sample 104. For example, the set of program instructions 116 may be programmed to cause the one or more processors 112 to identify a first set of a first care area, where the first care area is associated with a first design of interest within a block of repeating cells in design data, where the first care area has a first sensitivity threshold. By way of another example, the set of program instructions 116 may be programmed to cause the one or more processors 112 to identify an additional set of an additional care area, where the additional care area is associated with an additional design of interest within the block of repeating cells in design data, where the additional care area has an additional sensitivity threshold. By way of another example, the set of program instructions 116 may be programmed to cause the one or more processors 112 to receive one or more images of a selected region of a sample 104 from the inspection tool. By way of another example, the set of program instructions 116 may be programmed to cause the one or more processors 112 to identify one or more defects within the first set of the first care areas in the one or more images of the selected region of the sample 104 based on the first sensitivity threshold. By way of another example, the set of program instructions 116 may be programmed to cause the one or more processors 112 to identify one or more defects within the additional set of the additional care areas in the one or more images of the selected region of the sample 104 based on the additional sensitivity threshold. It is noted sensitivity thresholds of care areas are described in detail further herein.

In one embodiment, the one or more processors 112 of controller 110 include any one or more processing elements known in the art. In this sense, the one or more processors 112 may include any microprocessor device configured to execute algorithms and/or instructions. For example, the one or more processors 112 may consist of a desktop computer, mainframe computer system, workstation, image computer, parallel processor, vehicle on-board computer, handheld computer (e.g. tablet, smartphone, or phablet), or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. In general, the term "processor" may be broadly defined to encompass any device having one or more processing elements, which execute the program instructions 116 from a non-transitory memory medium (e.g., memory 114). Moreover, different subsystems of the system 100 (e.g., inspection tool 102 or user interface 120) may include processor or logic elements suitable for carrying out at least a portion of the steps described throughout the present disclosure. Therefore, the above description should not be interpreted as a limitation on the present invention but merely an illustration.

In one embodiment, the memory medium 114 of controller 110 includes any storage medium known in the art suitable for storing the program instructions 116 executable by the associated one or more processors 112. For example, the memory medium 114 may include a non-transitory memory medium. For instance, the memory medium 114 may include, but is not limited to, a read-only memory, a random access memory, a magnetic or optical memory device (e.g., disk), a magnetic tape, a solid state drive and the like. In another embodiment, it is noted herein that the memory 114 is configured to provide display information to a display device 122 and/or the output of the various steps described herein. It is further noted that memory 114 may be housed in a common controller housing with the one or more processors 112. In an alternative embodiment, the memory 114 may be located remotely with respect to the physical location of the processors 112 and controller 110. For instance, the one or more processors 112 of controller 110 may access a remote memory (e.g., server), accessible through a network (e.g., internet, intranet and the like). In another embodiment, the memory medium 114 stores the program instructions 116 for causing the one or more processors 112 to carry out the various steps described through the present disclosure.

In one embodiment, the display device 122 includes any display device known in the art. For example, the display device may include, but is not limited to, a liquid crystal display (LCD). By way of another example, the display device may include, but is not limited to, an organic light-emitting diode (OLED) based display. By way of another example, the display device may include, but is not limited to, a cathode-ray rube (CRT) display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with the user input device (e.g., touchscreen, bezel mounted interface, keyboard, mouse, trackpad, and the like) is suitable for implementation in the present invention.

In one embodiment, the user input device 124 includes any user input device known in the art. For example, user input device 124 may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface, those skilled in the art should recognize that a large number of touchscreen interfaces may be suitable for implementation in the present invention. For instance, the display device 122 may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of a display device is suitable for implementation in the present invention. In another embodiment, the user input device 124 may include, but is not limited to, a bezel mounted interface.

The embodiments of the system 100 illustrated in FIG. 1 may be further configured as described herein. In addition, the system 100 may be configured to perform any other steps(s) of any of the system and method embodiment(s) described herein.

FIGS. 2A-2C illustrates a cell 202 from a block of repeating cells in a set of design data 200, in accordance with the present disclosure. It is noted herein that the various system and method embodiments, components and architecture described previously herein should be interpreted to extend to the data 200 of FIG. 2.

In one embodiment, the design data 200 is analyzed to identify the electrical structure (e.g., SRAM block) of a semiconductor wafer and the potential location of one or more defects within the electrical structure. In another embodiment, the controller 110 selects the particular cell 202 from the block of repeating cells within the design data 200. In another embodiment, the cell 202 includes one or more designs of interest, where the one or more designs of interest correspond to potential locations for one or more defects. In another embodiment, the one or more designs of interest may be patterned. For example, the cell 202 may include a first patterned design of interest 201a. By way of another example, the cell 202 may include one or more additional patterned designs of interest 201b. In another embodiment, the particular cell 202 is displayed to the user. For example, the cell 202 may be displayed on the display 122 of the user interface 120. In another embodiment, the one or more designs of interest may be non-patterned (i.e., singular to the design data).

In another embodiment, one or more patterned designs of interest may be grouped into patterned regions. For example, the one or more patterned designs of interest may be grouped based on the amount of repeating present in the patterned designs of interest, the pattern complexity associated with the patterned designs of interest, and the orientation of the patterned designs of interest. It is noted herein that a given pattern region may also include non-patterned designs of interest (i.e., designs of interest singular to the design data). In another embodiment, as illustrated in FIG. 2B, two or more patterned designs of interest may be grouped together into a patterned region within cell 202.

In another embodiment, the controller 110 defines a first care area 204. For example, the first care area 204 may be defined to include a portion of one or more designs of interest within the cell 202. For instance, as shown in FIG. 2B, the first care area 204 encompasses a portion of a patterned design of interest 201a . In another embodiment, the first care area 204 is defined based on a portion of a patterned region within the cell 202 selected by a user via the user input 124 of the user interface 120. For example, where the user input 124 is a mouse cursor, the user may click and drag on the cell 202 to define a regular- or irregularly-shaped first care area 204. By way of another example, where the user input 124 is a stylus pen and touchpad, the user may draw on the cell 202 to define a regular- or irregularly-shaped first care area 204. In another embodiment, any repeats of the first care area 204 within the cell 202 are defined within the cell 202. For example, the controller 110 may automatically define repeats of the first care area 204 within the cell 202 via a series of program instructions. By way of another example, the user may manually define repeats of the first care area 204 within the cell 202.

In another embodiment, the controller 110 defines one or more additional care areas 206. For example, the one or more additional care areas 206 may be defined to include a portion of one or more designs of interest within the cell 202. For instance, as shown in FIG. 2C, a defined additional care area 206 encompasses a portion of the patterned design of interest 201a. In another embodiment, the one or more additional care areas 206 are less sensitive than the first care area 204, as described in detail further herein. In another embodiment, the one or more additional care areas 206 are defined based on a portion of the patterned region within the cell 202 selected by a user via the user input 124 of the user interface 120. For example, where the user input 124 is a mouse cursor, the user may click and drag on the cell 202 to define a regular- or irregularly-shaped one or more additional care areas 206. By way of another example, where the user input 124 is a stylus pen and touchpad, the user may draw on the cell 202 via a touchpad or the display 122 to define a regular- or irregularly-shaped one or more additional care areas 206. In another embodiment, any repeats of the one or more additional care areas 206 are defined within the cell 202. For example, the controller 110 may automatically define repeats of the one or more additional care areas 206 within the cell 202 via a series of program instructions. By way of another example, the user may manually define repeats of the one or more additional care areas 204 within the cell 202.

In another embodiment, the controller 110 performs a search function to apply the defined first care area 204 and the one or more additional care areas 206 to the remaining cells of the block of repeating cells within the design data 200. For example, the search function may be a pixel-to-design alignment function (PDA). Methods and systems for aligning design data to wafer inspection data are described in U.S. Pat. No. 7,676,077, issued on Mar. 9, 2010, which is incorporated herein by reference in the entirety.

In one embodiment, the defined first care area 204 has a corresponding first sensitivity threshold. In another embodiment, the defined one or more additional care areas 206 have a corresponding one or more additional sensitivity thresholds. In another embodiment, the first care area 204 has a higher sensitivity threshold than the one or more additional care areas 206. It is noted herein that the "sensitivity threshold" of a care area corresponds to the criticality of a defect in a care area of one or more images of a selected region of a sample. For example, a defect in a care area with a higher sensitivity threshold may be more critical to a wafer than a defect in a care area with a lower sensitivity threshold. It is further noted a care area with a higher sensitivity threshold is defined as being a "more sensitive" care area, for purposes of the present disclosure.

In another embodiment, the sensitivity threshold of a care area is defined by a number of comparison markers within the care area. For example, a lower number of comparison markers may correlate to a higher sensitivity threshold for the care area. In this example, a care area in the one or more images of the selected region of the sample missing one or more comparison markers may be identified as possessing a defect. For instance, where the first care area 204 has a higher sensitivity threshold than the one or more additional care areas 206, a lower number of comparison markers may be missing from the first care area 204 before a defect is identified, as compared to the number of comparison markers that may be missing from the one or more additional care areas 206 before a defect is identified.

By way of another example, a higher number of comparison markers may correlate to a higher sensitivity threshold for the care area. In this example, if a minimum number of comparison markers are not found within a care area in the one or more images of the selected region of the, that care area is identified as possessing a defect. For instance, where the first care area 204 has a higher sensitivity threshold than the one or more additional care areas 206, the first care area 204 must possess a higher number of comparison markers for a defect to not be identified, as compared to the number of comparison makers the one or more additional care areas 206 must possess.

Advantages of embodiments of the present disclosure include performing run-time context map (RTCM) rendering without having to define care areas during the inspection process by implementing PDA to align the cell 202 with first care area 204 and one or more additional care areas 206 to the remaining cells in the block of repeating cells within the design data 200. It is noted herein that RTCM rendering may be simplified by rendering horizontally, then vertically. Alternatively, RTCM rendering may be simplified by rendering vertically, then horizontally. Using an RTCM for the detecting step and/or any other steps described herein may be further performed as described in U.S. Pat. No. 7,676,077, issued on Mar. 9, 2010; U.S. Pat. No. 7,877,722, issued on Jan. 25, 2011; and U.S. Pat. No. 9,183,624, issued on Nov. 10, 2015, which are each incorporated herein by reference in the entirety.

Advantages of embodiments of the present disclosure also include allowing a user to render a care area array in design data according to the user's knowledge of where designs of interest may occur in the repeating structure instead of based on what is observed in the design data during the inspection process. It is noted herein that rendering the care area array according to the user's selections, instead of based on what is observed in the design data during the inspection process, may increase the sensitivity threshold of the care area array without sacrificing throughput speed of the inspection process, may afford for a higher adoption of tools implementing a user-defined care area array method, and may result in a greater ease of tool use. For example, implementing user-defined care areas during inspection instead of care areas rendered during the inspection process may reduce the computational expense required for RTCM rendering of the care area array, as it reduces the time spent to render care areas from design data during the inspection process.

FIG. 3 illustrates a process flow diagram depicting a method 300 for identifying one or more defects in a set of sample inspection images with one or more defined care areas in a set of design data. The method may also include any other step(s) that can be performed by the output acquisition subsystem and/or computer subsystem(s) or system(s) described herein. The steps may be performed by one or more computer systems, which may be configured according to any of the embodiments described herein. It is noted herein that the steps of method 300 may be implemented all or in part by the system 100. It is recognized, however, that the method 300 is not limited to the system 100 in that additional or alternative system-level embodiments may carry out all or part of the steps of method 300.

In a step 302, a particular cell from a block of repeating cells is displayed. In one embodiment, the controller 110 receives design data. In another embodiment, the design data includes a block of repeating cells. In another embodiment, a particular cell is selected from the block of repeating cells and is displayed. For example, the particular cell may be displayed on the display 122 of the user interface 120.

In a step 304, a first care area associated with a first design of interest is defined in the particular cell. In one embodiment, the first care area associated with a first design of interest is received from the user. For example, the first care area may be received from the user via the user input 124 of the user interface 120. In another embodiment, the first care area has a first sensitivity threshold, where the first sensitivity threshold is defined by the number of comparison markers in the first care area. For example, the number of comparison markers in the first care area may be 100. In another embodiment, a pattern search function is performed to apply the first care area to repeated instances of the associated first design of interest in the particular cell.

In a step 306, one or more additional care areas associated with one or more additional designs of interest are defined. In one embodiment, the one or more additional care areas associated with one or more additional designs of interest are received from the user. For example, the one or more additional care areas may be received from the user via the user input 124 of the user interface 120. In another embodiment, the one or more additional care areas have one or more additional sensitivity thresholds, where the one or more additional sensitivity threshold are defined by the number of comparison markers in the one or more additional care areas. For example, a second care area may have a second sensitivity threshold value of 200. By way of another example, the third care area may have a third sensitivity threshold value of 300. In another embodiment, the one or more additional care areas are less sensitive than the first care area (e.g., the one or more additional care areas have a lower sensitivity threshold than the first care area). In another embodiment, a pattern search function is performed to apply the one or more additional care areas to repeated instances of the associated one or more additional designs of interest in the particular cell.

In a step 308, the first care area and the one or more additional care areas are applied throughout the block of repeating cells. In one embodiment, a pattern search function is performed to apply the first care area to one or more additional occurrences of the first design of interest within the block of repeating cells. In another embodiment, a set of the first care area within the block of repeating cells is identified from the identified one or more additional occurrences of the first design of interest. In another embodiment, a pattern search function is performed to apply the one or more additional care areas to one or more additional occurrences of the one or more additional designs of interest within the block of repeating cells. In another embodiment, one or more additional sets of the one or more additional care areas with the block of repeating cells are identified from the identified one or more additional occurrences of the one or more additional design of interest.

In a step 310, one or more defects in one or more images of a selected region of a sample are identified. In one embodiment, one or more images of a selected region of a sample from the inspection tool are received. In another embodiment, the one or more defects are identified within the care areas in the one or more images of the sample. For example, one or more defects within the first set of care areas in the one or more images are identified based on the first sensitivity threshold. By way of another example, one or more defects within the one or more additional care areas of the one or more images are identified based on the one or more additional sensitivity thresholds.

It is noted herein up to an N number of care areas associated with up to an N number of designs of interest may be defined within the particular cell of the block of repeating cells. It is further noted herein the up to an N number of care areas associated with up to an N number of designs of interest may be received from the user. It is further noted herein the up to an N number of care areas may have up to an N number of sensitivity thresholds, where the up to an N number of sensitivity thresholds are defined by the number of comparison markers in the up to an N number of care areas. It is further noted herein a pattern search function may be performed to apply the up to an N number of care areas to repeated instances of the associated up to an N number of designs of interest in the particular cell. It is further noted herein a pattern search function may be performed to apply the up to an N number of care areas to up to an N number of occurrences of the up to an N number of designs of interest within the block of repeating cells. It is further noted herein that up to an N number of sets of up to an N number of care areas may be identified from the identified up to an N number of occurrences of the up to an N number of designs of interest. It is further noted herein that one or more defects within the up to an N number of care areas of the one or more images may be identified based on the up to an N number of sensitivity thresholds. Therefore, the above description should not be interpreted as a limitation on the present invention but merely an illustration.

It is noted herein that any of the defined sensitivity thresholds may be dependent or independent on the other defined sensitivity thresholds. It is further herein any of the pattern search functions embodied above may not be automated, but instead may be performed manually by the user. Therefore, the above description should not be interpreted as a limitation on the present invention but merely an illustration.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed:
1. A system, comprising:
an inspection tool, wherein the inspection tool includes a detector configured to acquire one or more images of a selected region of a sample;
a user interface, wherein the user interface includes a display and a user input device; and
a controller including one or more processors configured to execute a set of program instructions stored in memory, wherein the program instructions are configured to cause the one or more processors to:
receive design data, wherein the design data includes a block of repeating cells;
present, on the user interface, a particular cell of the block of repeating cells;
define a first care area associated with a first design of interest in the particular cell from a first input received via the user interface, wherein the first care area has a first sensitivity threshold;
define an additional care area associated with an additional design of interest in the particular cell from an additional input received via the user interface, wherein the additional care area has an additional sensitivity threshold, wherein the first care area is more sensitive than the additional care area;

identify a set of first care areas within the block of repeating cells by performing a search function to identify additional occurrences of the first design of interest within the block of repeating cells;

identify a set of additional care areas within the block of repeating cells by performing a search function to identify additional occurrences of the additional design of interest within the block of repeating cells;

configure the inspection tool based on the set of first care areas and the set of additional care areas to reduce inspection time when acquiring the one or more images of the selected region of the sample;

receive the one or more images of the selected region of the sample from the inspection tool;

identify one or more defects within the first set of care areas in the one or more images of the selected region of the sample based on the first sensitivity threshold; and identify one or more defects within the additional set of care areas in the one or more images of the selected region of the sample based on the additional sensitivity threshold.

2. The system in claim 1, wherein at least one of the first care area and the additional care area are defined based on a selection received by the controller via the user interface.

3. The system in claim 1, wherein the search function to identify additional occurrences of the first design of interest associated within the block of repeating cells includes a pixel-to-design alignment process.

4. The system in claim 1, wherein the search function to identify additional occurrences of the additional design of interest within the block of repeating cells includes a pixel-to-design alignment process.

5. The system in claim 1, wherein at least one of the identified set of first care areas within the block of repeating cells and the identified set of additional care areas within the block of repeating cells are utilized to perform run-time context map rendering.

6. The system in claim 1, wherein the first sensitivity threshold is determined by a plurality of comparison markers within the first care area, wherein a lower number of the plurality of comparison markers within the first care area corresponds to a higher sensitivity threshold for the first care area.

7. The system in claim 1, wherein the additional sensitivity threshold is determined by a plurality of comparison markers within the additional care area, wherein a lower number of the plurality of comparison markers within the additional care area corresponds to a higher sensitivity threshold for the additional care area.

8. The system in claim 1, wherein the first sensitivity threshold is higher than the additional sensitivity threshold.

9. The system in claim 1, wherein the inspection tool comprises at least one of a darkfield inspection tool or a brightfield inspection tool.

10. The system in claim 1, wherein the inspection system includes an illumination source.

11. The system in claim 10, wherein the illumination source comprises:
at least one of a narrowband source or a broadband source.

12. The system in claim 1, wherein the inspection tool comprises:
a scanning electron microscopy (SEM) tool.

13. A system, comprising:
a user interface, wherein the user interface includes a display and a user input device; and a controller including one or more processors configured to execute a set of program instructions stored in memory, wherein the program instructions are configured to cause the one or more processors to:

receive design data, wherein the design data includes a block of repeating cells;

present, on the user interface, a particular cell of the block of repeating cells;

define a first care area associated with a first design of interest in the particular cell from a first input received via the user interface, wherein the first care area has a first sensitivity threshold;

define an additional care area associated with an additional design of interest in the particular cell from an additional input received via the user interface, wherein the additional care area has an additional sensitivity threshold, wherein the first care area is more sensitive than the additional care area;

identify a set of first care areas within the block of repeating cells by performing a search function to identify additional occurrences of the first design of interest within the block of repeating cells;

identify a set of additional care areas within the block of repeating cells by performing a search function to identify additional occurrences of the additional design of interest within the block of repeating cells; and configure an inspection tool based on the set of first care areas and the set of additional care areas to reduce inspection time when acquiring the one or more images of the selected region of the sample, wherein the inspection tool includes a detector configured to acquire the one or more images of the selected region of the sample.

14. A system, comprising:
an inspection tool, wherein the inspection tool includes a detector configured to acquire one or more images of a selected region of a sample; and a controller including one or more processors configured to execute a set of program instructions stored in memory, wherein the program instructions are configured to cause the one or more processors to:

identify a set of first care areas, wherein a first care area is defined from a first input received via a user interface, wherein the first care area is associated with a first design of interest within a block of repeating cells in design data, wherein the first care area has a first sensitivity threshold, wherein the user interface includes a display and a user input device;

identify a set of additional care areas, wherein an additional care area is defined from an additional input received via the user interface, wherein the additional care area is associated with an additional design of interest within the block of repeating cells in design data, wherein the additional care area has an additional sensitivity threshold, wherein the first care area is more sensitive than the additional care area;

configure the inspection tool based on the set of first care areas and the set of additional care areas to reduce inspection time when acquiring the one or more images of the selected region of the sample;

receive the one or more images of the selected region of the sample from the inspection tool;

identify one or more defects within the first set of the first care areas in the one or more images of the selected region of the sample based on the first sensitivity threshold; and identify one or more defects within the additional set of the additional care areas in the one or more images of the selected region of the sample based on the additional sensitivity threshold.

15. A method comprising:

receiving design data, wherein the design data includes a block of repeating cells;

presenting, on a user interface, a particular cell of the block of repeating cells, wherein the user interface includes a display and a user input device;

defining a first care area associated with a first design of interest in the particular cell from a first input received via the user interface, wherein the first care area has a first sensitivity threshold;

defining an additional care area associated with an additional design of interest in the particular cell from an additional input received via the user interface, wherein the additional care area has an additional sensitivity threshold, wherein the first care area is more sensitive than the additional care area;

identifying a set of first care areas within the block of repeating cells by performing a search function to identify additional occurrences of the first design of interest within the block of repeating cells;

identifying a set of additional care areas within the block of repeating cells by performing a search function to identify additional occurrences of the additional design of interest within the block of repeating cells;

configuring an inspection tool based on the set of first care areas and the set of additional care areas to reduce inspection time when acquiring the one or more images of the selected region of the sample, wherein the inspection tool includes a detector configured to acquire the one or more images of the selected region of the sample;

receiving the one or more images of the selected region of the sample from the inspection tool;

identifying one or more defects within the first set of care areas in the one or more images of the selected region of the sample based on the first sensitivity threshold; and identifying one or more defects within the additional set of care areas in the one or more images of the selected region of the sample based on the additional sensitivity threshold.

16. The method in claim 15, wherein the first sensitivity threshold is determined by a plurality of comparison markers within the first care area, wherein a lower number of comparison markers within the first care area corresponds to a higher sensitivity threshold for the first care area.

17. The method in claim 15, wherein the additional sensitivity threshold is determined by a plurality of comparison markers within the additional care area, wherein a lower number of the plurality of comparison markers within the additional care area corresponds to a higher sensitivity threshold for the additional care area.

18. The method in claim 15, wherein the first sensitivity threshold is higher than the additional sensitivity threshold.

19. A method comprising:

receiving design data, wherein the design data includes a block of repeating cells;

presenting, on a user interface, a particular cell of the block of repeating cells, wherein the user interface includes a display and a user input device;

defining a first care area associated with a first design of interest in the particular cell from a first input received via the user interface, wherein the first care area has a first sensitivity threshold;

defining an additional care area associated with an additional design of interest in the particular cell from an additional input received via the user interface, wherein the additional care area has an additional sensitivity threshold, wherein the first care area is more sensitive than the additional care area;

identifying a set of first care areas within the block of repeating cells by performing a search function to identify additional occurrences of the first design of interest within the block of repeating cells;

identifying a set of additional care areas within the block of repeating cells by performing a search function to identify additional occurrences of the additional design of interest within the block of repeating cells; and configuring an inspection tool based on the set of first care areas and the set of additional care areas to reduce inspection time when acquiring the one or more images of the selected region of the sample, wherein the inspection tool includes a detector configured to the acquire one or more images of the selected region of the sample.

20. A method comprising:

identifying a set of first care areas, wherein a first care area is defined from a first input received via a user interface, wherein the first care area is associated with a first design of interest within a block of repeating cells in design data, wherein the first care area has a first sensitivity threshold, wherein the user interface includes a display and a user input device;

identifying a set of additional care areas, wherein an additional care area is defined from an additional input received via the user interface, wherein the additional care area is associated with an additional design of interest within the block of repeating cells in design data, wherein the additional care area has an additional sensitivity threshold, wherein the first care area is more sensitive than the additional care area;

configuring an inspection tool based on the set of first care areas and the set of additional care areas to reduce inspection time when acquiring the one or more images of the selected region of the sample, wherein the inspection tool includes a detector configured to acquire the one or more images of the selected region of the sample;

receiving the one or more images of the selected region of the sample from an inspection tool;

identifying one or more defects within the first set of the first care areas in the one or more images of the selected region of the sample based on the first sensitivity threshold; and identifying one or more defects within the additional set of the additional care areas in the one or more images of the selected region of the sample based on the additional sensitivity threshold.

* * * * *